(12) United States Patent
Tsai et al.

(10) Patent No.: US 10,481,037 B2
(45) Date of Patent: Nov. 19, 2019

(54) METHOD FOR DETECTING DETERIORATION DEFECT OF STRUCTURAL PART

(71) Applicant: INDUSTRIAL TECHNOLOGY RESEARCH INSTITUTE, Hsinchu (TW)

(72) Inventors: Yao-Long Tsai, Kaohsiung (TW); Li-Hua Wang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 202 days.

(21) Appl. No.: 15/855,944

(22) Filed: Dec. 27, 2017

(65) Prior Publication Data

US 2019/0017895 A1    Jan. 17, 2019

Related U.S. Application Data

(60) Provisional application No. 62/532,924, filed on Jul. 14, 2017.

(30) Foreign Application Priority Data

Nov. 24, 2017   (TW) .............................. 106140912 A (51) Int. Cl.
*G01M 3/28* (2006.01)
(52) U.S. Cl.
CPC ................................ *G01M 3/2807* (2013.01)
(58) Field of Classification Search
CPC ............................................. G01N 2291/0258
See application file for complete search history.

(56) References Cited

U.S. PATENT DOCUMENTS

| 5,184,516 A | 2/1993 | Blazic et al. |
| 6,880,379 B2 * | 4/2005 | Hedberg ................. G01N 3/30 |
| | | 702/38 |

(Continued)

FOREIGN PATENT DOCUMENTS

| CN | 104535323 A | 4/2015 |
| CN | 103049670 B | 8/2015 |

(Continued)

OTHER PUBLICATIONS

TW Office Action in application No. 107107654 dated Dec. 28, 2018.

(Continued)

*Primary Examiner* — Jennifer E Simmons
(74) *Attorney, Agent, or Firm* — Maschoff Brennan (57) ABSTRACT

A method for detecting deterioration of a structural part includes: detecting a waveform of time domain of the structural part by a sensor disposed on the structural part; performing a conversion of time domain to frequency domain for the waveform of time domain by a processor electrically connected to the sensor so as to obtain an actual modal parameter of each of a plurality of modals related to a waveform of frequency domain of the structural part; comparing the actual modal parameter of each of the plurality of modals to modal parameter information stored in a database to determine whether a deterioration defect exists in the structural part; and determining a degree and a position of the deterioration defect when the deterioration defect exists in the structural part.

10 Claims, 8 Drawing Sheets

(56) References Cited

U.S. PATENT DOCUMENTS

| | | |
|---|---|---|
| 8,296,083 B2 | 10/2012 | Martin |
| 8,640,544 B2 | 2/2014 | Lee et al. |
| 2006/0062343 A1 | 3/2006 | Pemg et al. |
| 2008/0294354 A1* | 11/2008 | Zhu .................. G01H 1/00 |
| | | 702/39 |
| 2012/0188078 A1 | 7/2012 | Soles et al. |
| 2014/0311245 A1* | 10/2014 | Horoshenkov ........ G01N 29/11 |
| | | 73/592 |
| 2015/0160169 A1 | 6/2015 | Hall et al. |
| 2015/0185186 A1 | 7/2015 | Han et al. |
| 2016/0146648 A1 | 5/2016 | Patel et al. |
| 2017/0030863 A1 | 2/2017 | Holmes et al. |

FOREIGN PATENT DOCUMENTS

| | | |
|---|---|---|
| TW | 198097 B | 1/1993 |
| TW | I243385 B | 11/2005 |
| TW | I449883 B | 8/2014 |
| TW | I572327 B | 3/2017 |

OTHER PUBLICATIONS

TW Office Action in application No. 107107654 dated Apr. 12, 2019.

"Artificial Neural Network for the Classification of Steel Hollow pipe", N mohamad, Hafizawati, R.A Siregar, M. Hariharan and Fauziah Mat, Proceedings of International Conference on Applications and Design in Mechanical Engineering (ICADME), Oct. 11-13, 2009.

"Detection of pipe wall-thinning based on change of natural frequencies of shell vibration modes", Soonwoo Han , Jinho Park , To Kang, 19thWorld Conference on Non-Destructive Testing 2016, Jul. 2016.

"Frequency-based experimental and theoretical identification of multiple cracks in straight pipes filled with fluid", S.M. Murigendrappa, S.K. Maiti, H.R. Srirangarajan, NDT&E International 37 (Feb. 20, 2004) 431-438.

"Identification of wall-thinning and cracks in pipes utilizing vibration modes and wavelets", M. El-Gebeily ,Y.A. Khulief, Applied Mathematical Modelling 40 (Dec. 14, 2015) 5335-5348.

"Inexpensive Pipelines Health Evaluation Techniques Based on Resonance Determination", Numerical Simulation and Experimental Testing, Waheed Sami Abushanab, Engineering, Mar. 27, 2013, 5, 337-343.

TW Office Action dated Jun. 19, 2018 as received in Application No. 106140912.

* cited by examiner

METHOD FOR DETECTING DETERIORATION DEFECT OF STRUCTURAL PART

CROSS-REFERENCE TO RELATED APPLICATIONS

This non-provisional application claims priority under 35 U.S.C. § 119(a) on Patent Application No(s). 106140912 filed in Taiwan, R.O.C. on Nov. 24, 2017, claims priority under 35 U.S.C. § 119(e) on Provisional Application No(s). 62/532,924 filed in U.S. on Jul. 14, 2017, the entire contents of which are hereby incorporated by reference.

TECHNICAL FIELD

The disclosure relates to method for detecting a deterioration defect of a structural part.

BACKGROUND

Recently, the frequency of occurrence of accidents involving domestic industrial pipelines increases. When industrial pipelines leak due to abnormalities, it leads to serious disasters, such as casualties and property damage. The main cause of anomalies in industrial pipelines is human-induced factors, and secondly material deterioration in pipelines or equipment. In order to avoid such disasters, full-time monitoring of industrial pipelines is considered as a priority. Although manufacturers of various countries have developed a monitoring system in this regard, the concept of the monitoring system is based on a monitoring of process parameters, an analysis of operating status and performance and still lacks the capabilities of detecting deterioration. In other words, this type of monitoring system only detects when the pipeline is damaged and leaks, and fails to meet the demands of the safety operation of factories and the reduction of risks.

The main technical shortcomings of the present industrial pipeline safety monitoring are summarized as follows. First, the environmental sensors or process parameters sensors set up at the site are used for the process monitoring to regulate the production process, and it lacks appropriate safety diagnosis modules for the logical judgment analysis. Second, it lacks the monitoring technology of sensing deterioration remotely, and commonly used non-destructive detection technology is only applicable to the position of partial pipeline where the sensors are disposed. This type of detection technology can only be used for detecting when the pipeline is broken and fluid leaks, and it is impossible to send out an early warning signal in the event of deterioration. Third, the operating environment of industrial plants varies with the system, structure and components. The sensors must have the durability to overcome the problems of high temperature and high humidity environment as well as long-term monitoring. In other words, it is not easy to instantaneously detect damage or deterioration of the pipeline due to the limitations of the conventional pipeline inspection methods and technique. Accordingly, the proper time for immediately performing maintenance and dealing with contingency is missed. Therefore, in the field of industrial safety, it is necessary to develop technologies related to diagnosis and monitoring so as to establish a complete monitoring system for the issue of pipeline safety.

SUMMARY

A method for detecting deterioration defect of a structural part is disclosed according to one embodiment of the present disclosure. The method includes the following steps: detecting a waveform of time domain of the structural part by a sensor disposed on the structural part; performing a conversion of time domain to frequency domain for the waveform of time domain by a processor electrically connected to the sensor so as to obtain an actual modal parameter of each of a plurality of modals related to a waveform of frequency domain of the structural part; comparing the actual modal parameter of each of the plurality of modals to modal parameter information stored in a database to determine whether a deterioration defect exists in the structural part; and determining a degree and a position of the deterioration defect when the deterioration defect exists in the structural part; wherein the modal parameter information comprises sets of comparison modal parameters, and each of the sets of comparison modal parameters indicates a respective one of the deterioration defect of the position and other deterioration defects of other positions in the structural part.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
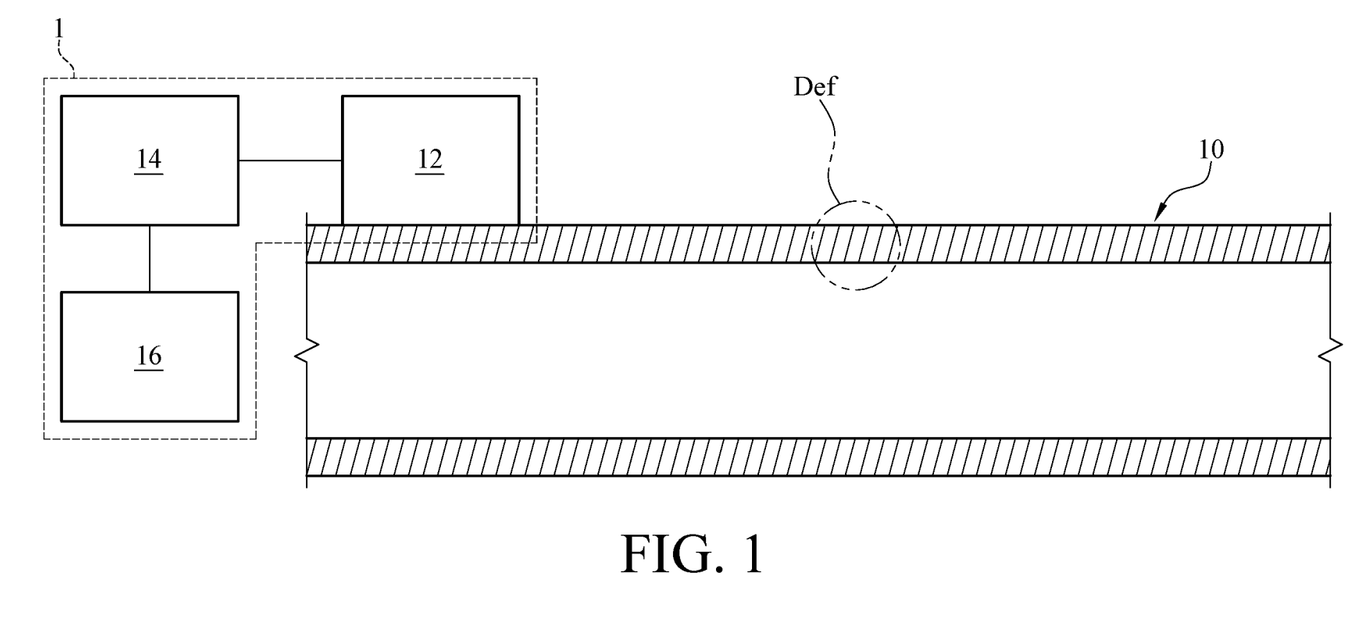
FIG. 1 is a diagram of a structural part and a system for detecting a deterioration defect of the structural part according to one embodiment of the present disclosure.
Figure 2:
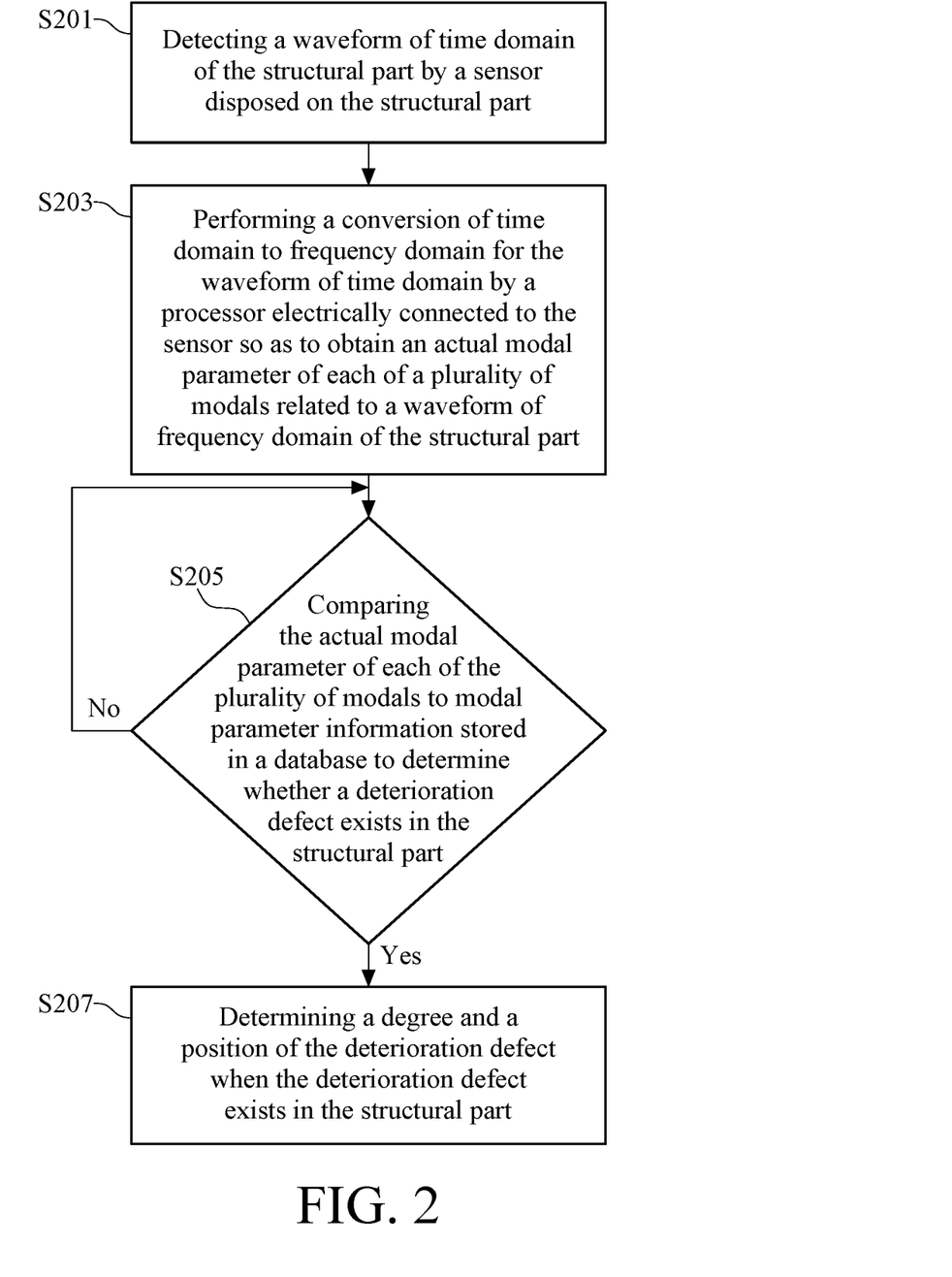
FIG. 2 is a diagram of a flow chart illustrating a method for detecting a deterioration defect of the structural part according to one embodiment of the present disclosure.

Please refer to FIG. 1 and FIG. 2. FIG. 1 is a diagram of a structural part and a system for detecting a deterioration defect of the structural part according to one embodiment of the present disclosure, and FIG. 2 is a diagram of a flow chart illustrating a method for detecting a deterioration defect of the structural part according to one embodiment of the present disclosure. As shown in said figures, a detection system 1 for detecting deterioration defect includes a sensor 12, a processor 14 and a database 16. In the detection system and method for detecting a deterioration defect applied to a structural part 10, first of all, a sensor 12 is disposed on the structural part 10 to be detected, the sensor 12 is electrically connected to the processor 14, and the processor 14 is connected to the database 16 which is built up in advanced so as to complete the structure of the system for detecting the deterioration defect 1. Then, the structural part is excited so that a time domain waveform of the structural part 10 is detected by the sensor 12 disposed on the structural part 10, as shown in step S201. The structural part 10 of the present disclosure is described as a pipeline for illustration. However, in other embodiments, the structural part 10 is other industrial equipment such as a tankage, and the present disclosure is not limited to the above embodiment in which the structural part is described as a pipeline. In practice, the method for detecting the deterioration defect of the structural part further includes generating the waveform of time domain by an excitation source or fluid flowing through the structural part 10 before detecting the waveform of time domain of the structural part 10 by the sensor disposed on the structural part. In other words, in practice, a vibration of the structural part 10, which leads to the waveform of time domain, is caused by sending a signal to the structural part using an excitation source or by providing fluid to flow through the structural part.

Figure 3:
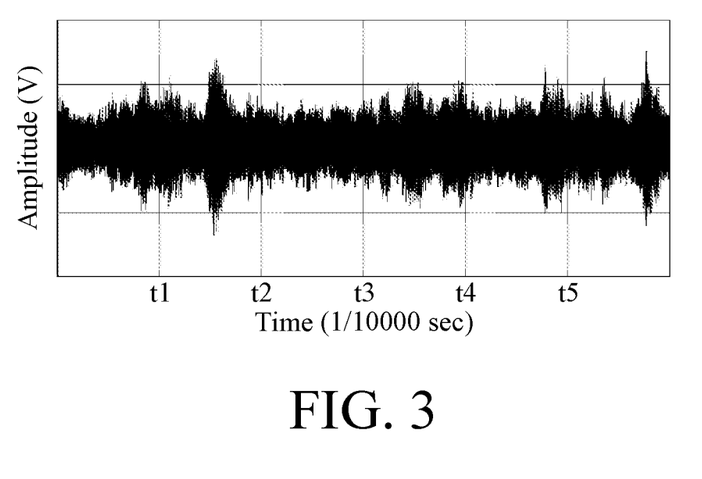
FIG. 3 is a diagram of a waveform of time domain of the structural part according to one embodiment of the present disclosure.
Figure 4:
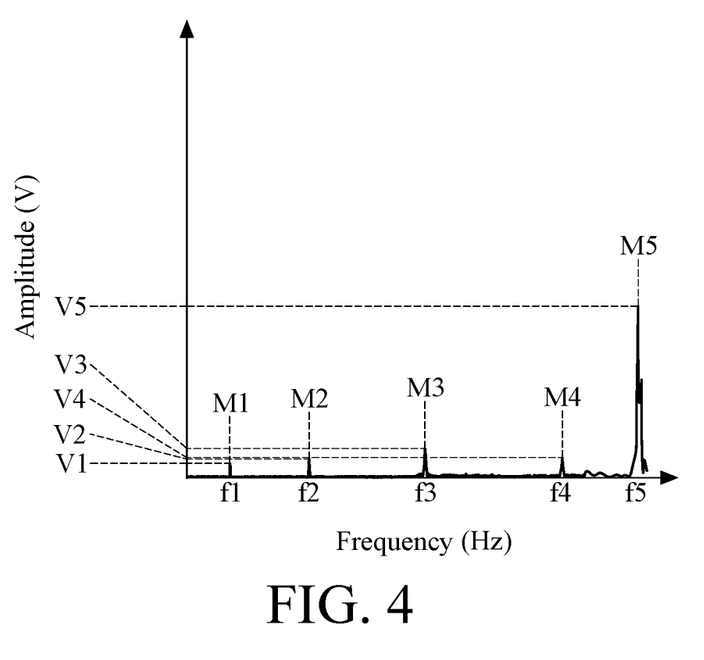
FIG. 4 is a diagram of a waveform of frequency domain of the structural part according to one embodiment of the present disclosure.

Please further refer to FIG. 3 and FIG. 4. FIG. 3 is a diagram of a waveform of time domain of the structural part according to one embodiment of the present disclosure. FIG. 4 is a diagram of a waveform of frequency domain of the structural part according to one embodiment of the present disclosure. As shown in FIG. 3, the sensor 12 detects the waveform of time domain of the structural part 10 when the structural part 10 vibrates, and the sensor 12 further sends the waveform of time domain to the processor 14. Then, in step S203, the processor 14, electrically connected to the sensor 12, performs a conversion of time domain to frequency domain for the waveform of time domain so as to obtain an actual modal parameter of each of a plurality of modals related to a waveform of frequency domain of the structural part 10. As shown in the embodiment of FIG. 4, the waveform of frequency domain includes a plurality of modals M1-M5. In practice, the conversion of time domain to frequency domain is a Fast Fourier Transform (FFT), a Hilbert-Huang Transform (HHT) or a Wavelet Analysis, etc.

Then, in step S205, the processor 14 compares the actual modal parameter of each of the plurality of modals M1-M5 to modal parameter information stored in the database 16 to determine whether a deterioration defect exists in the structural part 10, such as the deterioration defect Def shown in FIG. 1. In step S207, the processor 14 further determines a degree and a position of the deterioration defect when the deterioration defect exists in the structural part. In this embodiment, the modal parameter information includes sets of comparison modal parameters, and each of the sets of comparison modal parameters indicates a respective one of the deterioration defect of the position and other deterioration defects of other positions in the structural part 10.

Figure 5:
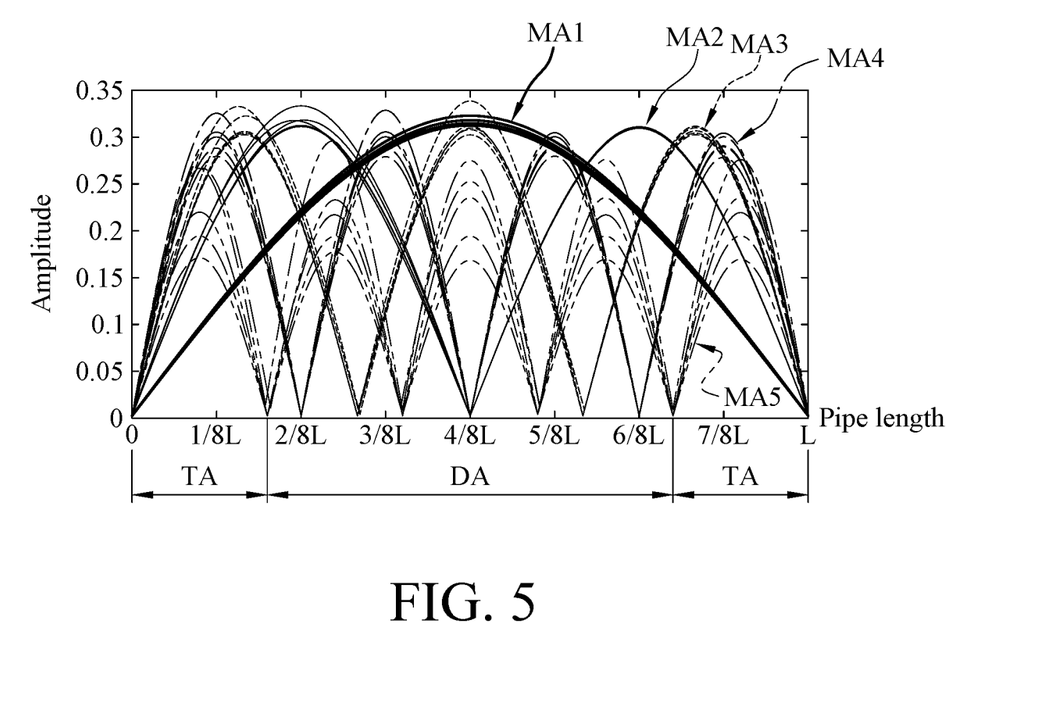
FIG. 5 is diagram of waveform of sets of comparison modal parameters stored in the database according to one embodiment of the present disclosure.

Please refer to FIG. 1, FIG. 4 and FIG. 5. FIG. 5 is a diagram of waveform of sets of comparison modal parameters stored in the database according to one embodiment of the present disclosure. In this embodiment, the actual modal parameter of each modal includes an amplitude value of a characteristic frequency (natural frequency), and each of the sets of comparison modal parameters corresponds to a plurality of first deterioration curves. As shown in FIG. 4 and FIG. 5, the actual modal parameters of each of the modals M1-M5 includes a respective one of the characteristic frequency f1-f5, and each of the comparison modal parameters MA1-MA5 correspond to a plurality of first deterioration curves. Each of the plurality of first deterioration curves corresponds to a predicted deterioration defect having a deterioration defect value and located in a position of the structural part 10. Step S207, determining the degree and the position of the deterioration defect, comprises comparing each of the amplitude values of the characteristic frequencies to the plurality of first deterioration curves of a respective one of the sets of comparison modal parameters, so as to determine the degree and the position of the deterioration defect. Specifically, the processor 14 knows an amplitude value of a characteristic frequency of an actual modal parameter when obtaining the actual modal parameter of a modal of the structural part 10. For example, as shown in FIG. 4, the actual modal parameter of the modal M1 includes an amplitude value V1 of a characteristic frequency f1 and the actual modal parameter of the modal M2 includes an amplitude value V2 of a characteristic frequency f2, etc. In this embodiment, each of the comparison modal parameters MA1-MA5 corresponds to a respective one of the modals M1-M5 of the structural part 10.

The modal M1 is illustrated as an example in the following paragraph. When the processor 14 obtains the amplitude value V1 of the characteristic frequency f1 of the modal M1, the processor 14 is capable of finding out a respective first deterioration curve among the plurality of first deterioration curves included in the comparison modal parameters MA1 among the sets of comparison modal parameters stored in the database 16, as shown in FIG. 5, according to the disposing position of the sensor 12 on the structural part 10 as well as the amplitude value V1. The degree of deterioration defect value of the predicted deterioration defect and the position where the predicted deterioration defect is located corresponding to the first deterioration curve indicates the degree and the position of the deterioration defect of the structural part 10. In an example, due to the disposing position of the sensor 12 in the structural part 10, the processor 14 is not capable of obtaining the first deterioration curve corresponding to the amplitude value by comparison, so that the processor 14 may not find out the degree and the position of the deterioration defect of the structural part 10. Therefore, more modals of the structural part 10 are applied for comparison in FIG. 5, more accurate the degree and the position of the deterioration defect of the structural part 10 found are and the aforementioned problem is avoided.

The system for detecting deterioration defect 1 is not capable of obtaining the first deterioration curve of the structural part 10 through the amplitude value due to the limitation of the disposing position of the sensor 12 on the structural part 10 when using the amplitude value of the characteristic frequency shown in FIG. 5 to detect the degree and the position of the deterioration defect. Thereby, the degree and the position of the deterioration defect of the structural part 10 are not determined. For example, as shown in FIG. 5, when the sensor 12 is disposed in the node interference area DA, the processor 14 is not capable of determining which one of the plurality of first deterioration curves corresponds to the degree and the position of the deterioration defect of the structural part 10 because the amplitude value is located on the same node of the plurality of first deterioration curves. Accordingly, in one embodiment, before detecting the waveform of time domain of the structural part 10 by the sensor 12 disposed on the structural part 10, the method further includes determining the disposing position of the sensor 12 on the structural part 10 according to a characteristic frequency of each of the sets of comparison modal parameters of the database 16. In the embodiments of FIG. 1 and FIG. 5, the processor 14 predicts an ideal disposing position of the sensor 12 according to the characteristic frequency of each of the comparison modal parameters stored in the database 16 built up in advanced. In a preferred embodiment, a distance exists between the disposing position of the sensor 12 and one end of the structural part 10, and the distance is less than or equal to ½ length of the wavelength corresponding to the characteristic frequency having a greatest frequency value among the characteristic frequencies. Therefore, as shown in the embodiment of FIG. 5, the comparison modal parameter MA5 among the comparison modal parameters MA1-MA5 has the greatest characteristic frequency and the processor 14 determines the ideal disposing position of the sensor 12 as a measurement area TA according to the wavelength of the characteristic frequency having the greatest frequency value included in the comparison modal parameter MA5. In other words, an engineer may dispose the sensor 12 on the position spaced apart from either one of the two ends of the structural part 10 at the distance of ½ wavelength according to the determination of the processor 14. Thereby, the problem that the processor 14 is not capable of obtaining the degree and the position of the deterioration defect of the structural part 10 due to the disposing position of the sensor 12 located in the node interference area DA of the structural part 10 is avoided.

Figure 6:
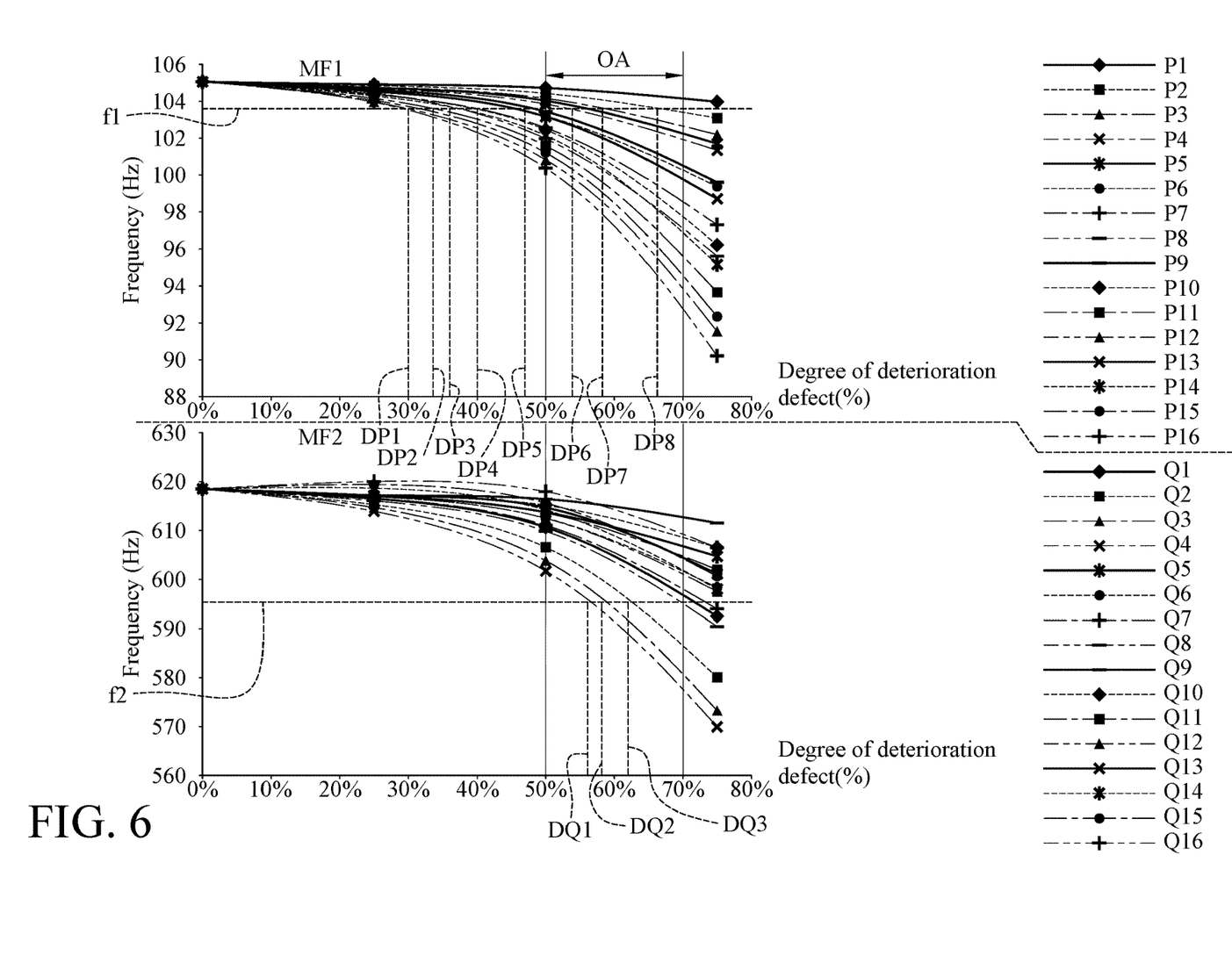
FIG. 6 is diagram of waveform of the sets of comparison modal parameters stored in the database according to another embodiment of the present disclosure.
Figure 7:
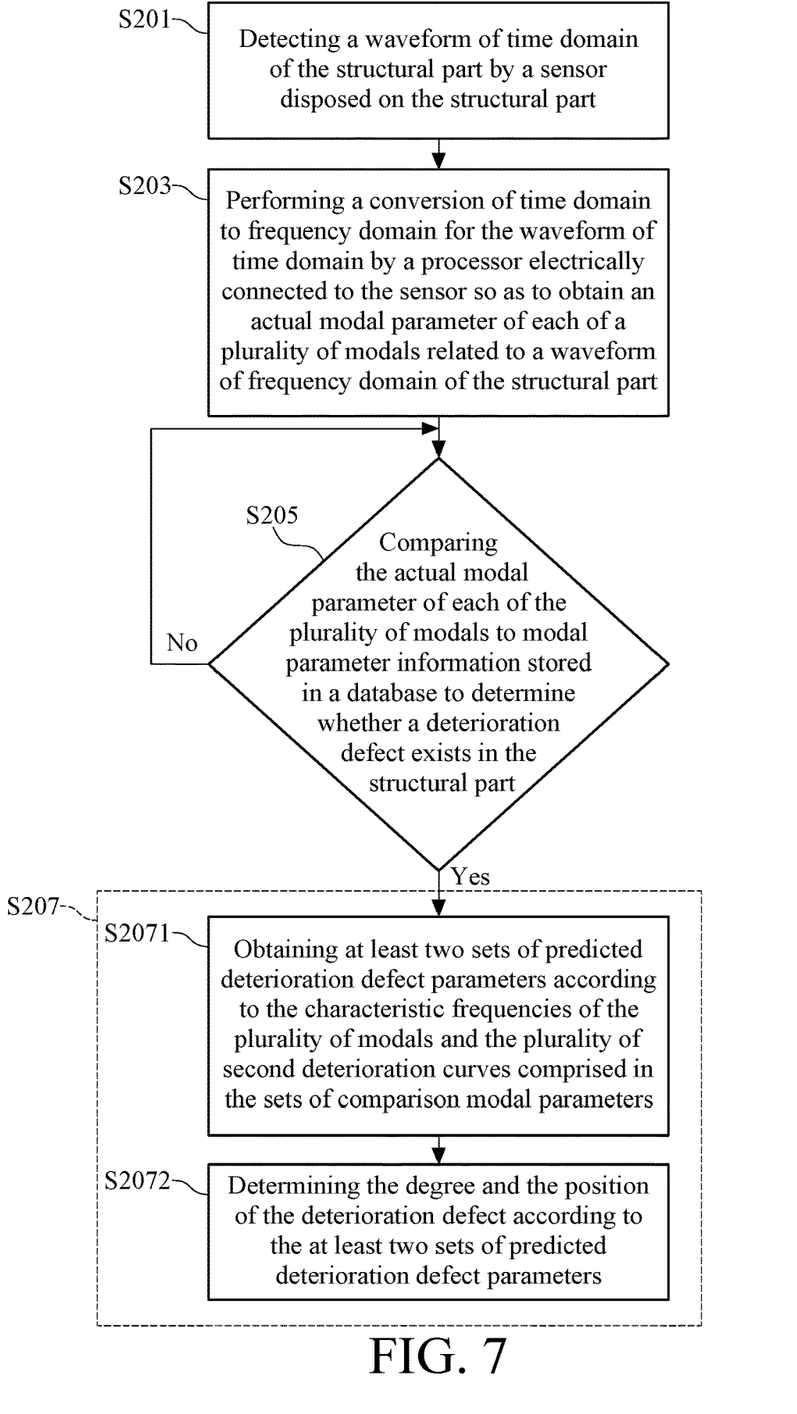
FIG. 7 is a flow chart illustrating a method for detecting a deterioration defect of the structural part according to another embodiment of the present disclosure.

The aforementioned embodiment of FIG. 5 is given for illustrating the degree and the position of the deterioration defect of the structural part 10 obtained from the comparison using the amplitude value of the same characteristic frequency. In another embodiment, the degree and the position of the deterioration defect of the structural part 10 are obtained based on the comparison regarding the variation of the characteristic frequency. Please refer to FIG. 1, FIG. 4 and FIG. 6. FIG. 6 is a diagram of waveform of the sets of comparison modal parameters stored in the database according to another embodiment of the present disclosure. In this embodiment, the actual modal parameter of each of the modals of the structural part 10 includes a characteristic frequency, such as frequencies f1 and f2, and each of the comparison modal parameters MF1 and MF2 includes a plurality of second deterioration curves, such as the second deterioration curves P1-P16 and Q1-Q16, as shown in FIG. 6. Please further refer to FIG. 7, which is a flow chart illustrating a method for detecting a deterioration defect of the structural part according to another embodiment of the present disclosure. The embodiment of FIG. 7 is similar to the embodiment of FIG. 2. The only significant difference between FIG. 7 and FIG. 2 lies in that step S207 of FIG. 7, indicating that the processor determines the degree and the position of the deterioration defect, includes step S2071 and S2072. In step S2071, the processor 14 obtains at least two sets of predicted deterioration defect parameters according to the characteristic frequencies of the plurality of modals and the plurality of second deterioration curves included in the sets of comparison modal parameters. Then, in step S2072, the processor 14 determines the degree and the position of the deterioration defect according to the at least two sets of predicted deterioration defect parameters.

The embodiment of FIG. 6 is given for illustration. FIG. 6 shows two sets of comparison modal parameters MF1 and MF2. The comparison modal parameter MF1 includes a plurality of second deterioration curves P1-P16, and the comparison modal parameter MF2 includes a plurality of second deterioration curves Q1-Q16. Each of the second deterioration curves indicates the degree of a deterioration defect corresponding to a length and a position of the deterioration defect at a variety of frequencies. For example, the second deterioration curve Q1 indicates the degrees of a deterioration defect of the structural part 10 having a length of 50 mm of the deterioration defect located in a position of ⅛ pipe length at a variety of frequencies. In another example, the second deterioration curve Q7 indicates the degrees of a deterioration defect of the structural part 10 having a length of 150 mm of the deterioration defect located in a position of ⅜ pipe length at a variety of frequencies.

In this embodiment, assume that the modals M1 and M2 of the structural part 10 obtained by the processor 14 respectively correspond to the set of comparison modal parameters MF1 and MF2 stored in the database 16, and the actual modal parameter of the modal M1 and the actual modal parameter of the modal M2 respectively includes the characteristic frequency f1 and the characteristic frequency f2. The processor 14 searches for possible degree and position of the deterioration defect of the structural part 10 according to the characteristic frequency f1 and the second deterioration curves P1-P16 included in the set of comparison modal parameters MF1 stored in the database 16. As shown in FIG. 6, the processor 14 obtains a set of deterioration defect parameters including the deterioration defect parameters DP1-DP8 from the set of comparison modal parameters MF1. Similarly, the processor 14 obtains a set of deterioration defect parameters including the deterioration defect parameters DQ1-DQ3 from the set of comparison modal parameters MF2. The processor 14 determines possible degree and position of the deterioration defect of the structural part 10 according to the deterioration defect parameters DP1-DP8 and the deterioration defect parameters DQ1-DQ3.

More specifically, in one embodiment, the step that the processor 14 determines the degree and the position of the deterioration defect according to the at least two sets of predicted deterioration defect parameters includes filtering out at least one predicted deterioration defect parameter repeated by comparing the at least two sets of predicted deterioration defect parameters, and the at least one predicted deterioration defect parameter is related to the degree and the position of the deterioration defect. In this embodiment, the processor 14 filters out the predicted deterioration defect parameters repeated, which are predicted deterioration defect parameters DQ1-DQ3, by comparing the set of predicted deterioration defect parameters DP1-DP8 and the set of predicted deterioration defect parameters DQ1-DQ3. Thereby, the processor 14 determines that the degree and the position of the deterioration defect of the structural part 10 are respectively the degree and the position of the deterioration defect corresponding to one of the predicted deterioration defect parameters DQ1-DQ3.

In practice, in order to determine the degree and the position of the deterioration defect more accurately, the processor 14 obtains a set of predicted deterioration defect parameters other than the above two sets of predicted deterioration defect parameters further according to a characteristic frequency included in an actual modal parameter of a modal other than the aforementioned modal M1 and M2, as well as a set of comparison modal parameters other than the aforementioned set of comparison modal parameters MF1 and MF2. Then, the processor 14 further compares the set of predicted deterioration defect parameters to the above two sets of predicted deterioration defect parameters to filter out at least one predicted deterioration defect parameter repeated. In other words, the more characteristic frequencies of modals the processor 14 obtains, the more accurately the processor 14 is capable of determining the degree and the position of the deterioration defect of the structural part 10. In one embodiment, the comparison modal parameter MF1 and MF2 are obtained in their own respective time. For example, the comparison modal parameter MF1 is obtained in a first time, and the comparison modal parameter MF2 is obtained in a second time. The embodiments of FIG. 5 and FIG. 6 are given for illustrating the techniques of determining the degree and the position of the deterioration defect of the structural part 10 based on the variations of frequencies or the variations of amplitudes of the frequencies. In other words, in the spirit of the present disclosure, due to the physical feature of the natural frequency of the structural part, the partial rigidity and mass of the structural part change with a deterioration defect existing in the structural par, so that the degree and the position of the deterioration defect are determined accordingly. Thereby, a set of technologies for monitoring deterioration defects of a structural part is developed without damaging the structural part, so as to ensure the safety of operation of the structural part such as an industrial pipeline or an industrial tank and further to prevent people from working in a high-risk environment.

Figure 8:
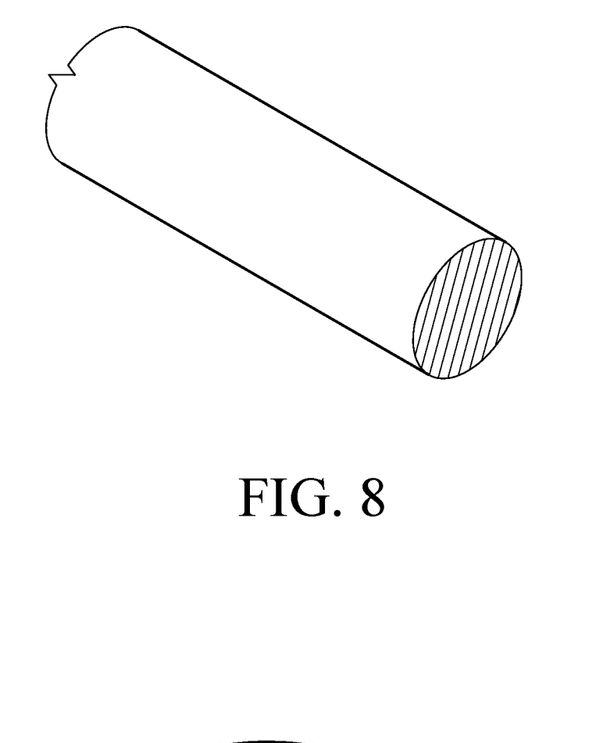
FIG. 8 to FIG. 11 are respectively diagrams illustrating stereoscopic views of structural parts having different forms.

The technical ideas of the system and the method for detecting the deterioration defect of the structural part of the present disclosure are adapted to a variety of structural parts with different forms. For example, please refer to FIG. 8 to FIG. 11, which are respectively diagrams illustrating stereoscopic views of structural parts having different forms. As shown in FIG. 8 to FIG. 11, the structural part adapted to the system and the method of the present disclosure has a form of solid cylinder, bent tube, square tube and I-section. In the embodiment of FIG. 8 showing the form of solid cylinder, assume the pipe length of the structural part is L, and the degrees (% pipe thickness) of the deterioration defect of the structural part as well as characteristic frequency (Hz) variations at ¼L and ½L in different modals M1-M5 are shown in Table 1 and Table 2.

TABLE 1

| ¼L | M1 | M2 | M3 | M4 | M5 |
|---|---|---|---|---|---|
| 0% | 22.05239 | 60.7595 | 119.0305 | 196.5821 | 293.3228 |
| 25% | 21.67752 | 58.70199 | 116.0998 | 195.5517 | 292.006 |
| 50% | 20.77782 | 54.38835 | 111.2858 | 193.6701 | 289.0152 |
| 75% | 18.47006 | 47.43438 | 105.8418 | 190.2872 | 282.3232 |

TABLE 2

| ½L | M1 | M2 | M3 | M4 | M5 |
|---|---|---|---|---|---|
| 0% | 22.05239 | 60.7595 | 119.0305 | 196.5821 | 293.3228 |
| 25% | 21.08352 | 60.7286 | 116.2668 | 196.3019 | 287.4922 |
| 50% | 18.96757 | 60.63222 | 111.1252 | 195.4105 | 279.0904 |
| 75% | 15.04959 | 60.32965 | 104.5329 | 192.6023 | 271.1687 |

Figure 9:
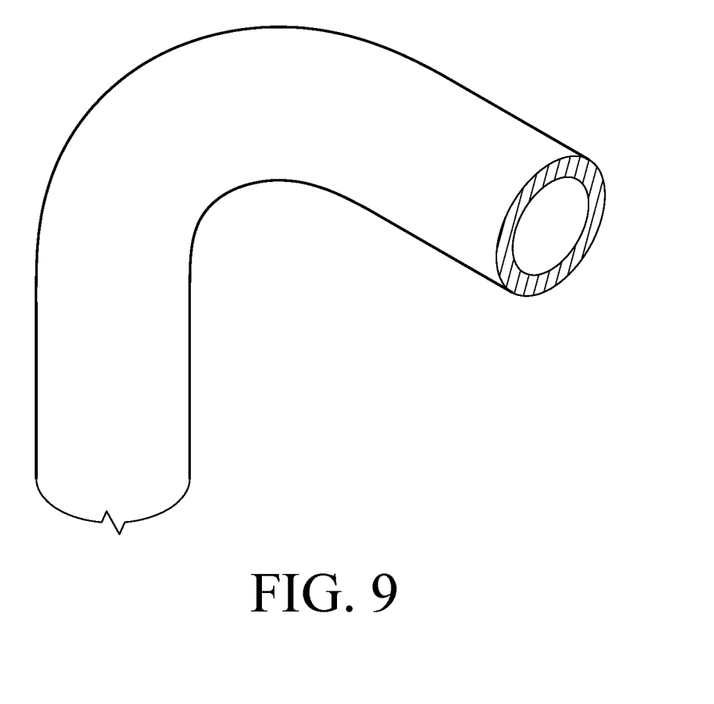

In the embodiment of FIG. 9 showing the form of bent tube, assume the pipe length of the structural part is L, and the degrees (% pipe thickness) of the deterioration defect of the structural part as well as characteristic frequency (Hz) variations at ¼L and ½L in different modals M1-M5 are shown in Table 3 and Table 4.

TABLE 3

| ¼L | M1 | M2 | M3 | M4 | M5 |
|---|---|---|---|---|---|
| 0% | 107.6097 | 299.3441 | 576.457 | 912.6012 | 1229.042 |
| 25% | 107.0839 | 296.2418 | 571.8002 | 908.6208 | 1227.168 |
| 50% | 105.9831 | 289.5574 | 561.6209 | 900.6288 | 1222.553 |
| 75% | 102.8482 | 272.4134 | 538.6506 | 881.1895 | 1208.208 |

TABLE 4

| ½L | M1 | M2 | M3 | M4 | M5 |
|---|---|---|---|---|---|
| 0% | 107.6097 | 299.3441 | 576.457 | 912.6012 | 1229.042 |
| 25% | 105.8333 | 295.0557 | 574.2221 | 910.5367 | 1222.309 |
| 50% | 102.1406 | 283.489 | 567.4657 | 905.5377 | 1212.337 |
| 75% | 92.93562 | 264.4272 | 549.8736 | 889.8458 | 1207.469 |

Figure 10:
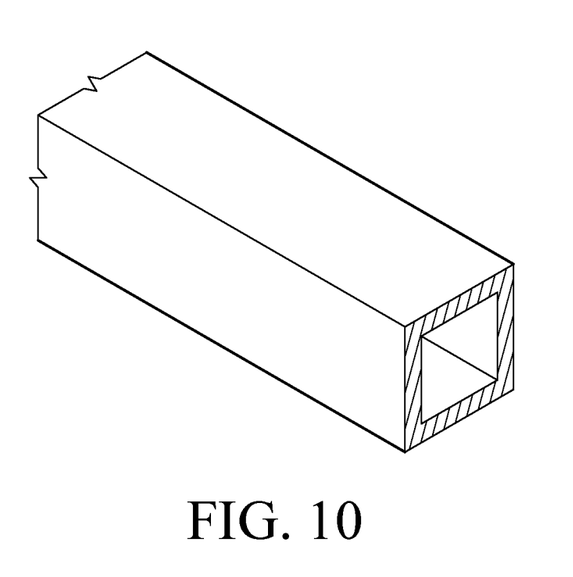

In the embodiment of FIG. 10 showing the form of square tube, assume the pipe length of the structural part is L, and the degrees (% pipe thickness) of the deterioration defect of the structural part as well as characteristic frequency (Hz) variations at ¼L and ½L in different modals M1-M5 are shown in Table 5 and Table 6.

TABLE 5

| ¼L | M1 | M2 | M3 | M4 | M5 |
|---|---|---|---|---|---|
| 0% | 79.61369 | 217.4225 | 420.4544 | 682.7447 | 998.1407 |
| 25% | 78.88281 | 214.2276 | 416.3346 | 680.6828 | 995.8001 |
| 50% | 77.32048 | 206.8515 | 407.3621 | 675.946 | 989.165 |
| 75% | 72.86193 | 189.1832 | 389.8823 | 624.6216 | 968.927 |

TABLE 6

| ½L | M1 | M2 | M3 | M4 | M5 |
|---|---|---|---|---|---|
| 0% | 79.61369 | 217.4225 | 420.4544 | 682.7447 | 998.1407 |
| 25% | 78.00208 | 217.2905 | 417.5578 | 679.9839 | 993.1377 |
| 50% | 74.25027 | 216.9309 | 409.6331 | 646.52 | 981.6498 |
| 75% | 64.82471 | 215.732 | 391.9877 | 565.5287 | 960.5893 |

Figure 11:
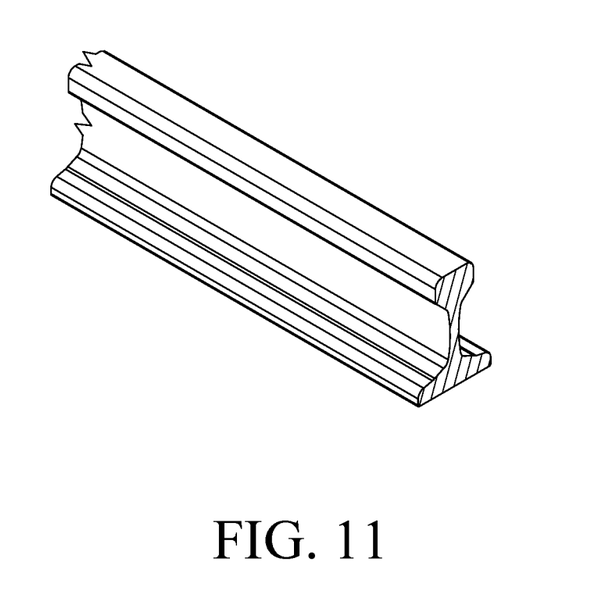

In the embodiment of FIG. 11 showing the form of I-section, assume the pipe length of the structural part is L, and the degrees (% pipe thickness) of the deterioration defect of the structural part as well as characteristic frequency (Hz) variations at ¼L and ½L in different modals M1-M5 are shown in Table 7 and Table 8.

TABLE 7

| ¼L | M1 | M2 | M3 | M4 | M5 |
|---|---|---|---|---|---|
| 0% | 219.8807 | 561.3934 | 1001.138 | 1492.311 | 2007.315 |
| 25% | 219.0764 | 557.3356 | 995.5444 | 1490.648 | 2006.844 |
| 50% | 217.4524 | 549.2907 | 984.642 | 1486.917 | 2003.783 |
| 75% | 211.2352 | 536.2614 | 967.8168 | 1481.157 | 1997.218 |

TABLE 8

| ½L | M1 | M2 | M3 | M4 | M5 |
|---|---|---|---|---|---|
| 0% | 219.8807 | 561.3934 | 1001.138 | 1492.311 | 2007.315 |
| 25% | 217.679 | 561.4051 | 996.8888 | 1492.386 | 2000.988 |
| 50% | 210.4497 | 561.2004 | 987.3976 | 1491.165 | 1990.76 |
| 75% | 199.0602 | 560.656 | 970.7511 | 1488.125 | 1978.935 |

In one embodiment, the actual modal parameter of each modal includes a characteristic frequency, and the characteristic frequency has a first frequency in a first direction and a second frequency in a second direction. The method for detecting the deterioration defect further includes determining a form of the deterioration defect according to the first frequency in the first direction and the second frequency in the second direction. Specifically, in this embodiment, the sensor 12 of the present disclosure is a three-axis accelerometer sensor used for detecting frequencies in a variety of directions, such as the frequency in the X axis direction and the frequency in the Y axis direction. The processor 14 determines the form of the deterioration defect of structural part 10 according to the variation of the frequency in the X axis direction and the variation of the frequency in the Y axis direction. The form of deterioration defect is, for example, a uniform defect or a partial defect. In detailed, in one embodiment, the step of determining the form of the deterioration defect according to the first frequency in the first direction and the second frequency in the second direction by the processor 14 includes the step of determining whether the first frequency in the first direction is consistent with the second frequency in the second direction. The form of the deterioration defect is determined as a uniform defect by the processor 14 when the first frequency in the first direction is consistent with the second frequency in the second direction. The form of the deterioration defect is determined as a partial defect by the processor 14 when the first frequency in the first direction is not consistent with the second frequency in the second direction.

In one embodiment, the database 16 is a partial-defect database or a uniform-defect database, and the method for detecting deterioration defect of the structural part 10 further includes determining whether the database 16 is the partial-defect database or the uniform-defect database according to the form of the deterioration defect. More specifically, in a practical example, in the method for detecting the deterioration defect of the structural part, the processor 14 determines the form of the deterioration defect according to a first frequency in a first direction and a second frequency in a second direction. When the deterioration defect of the structural part 10 is determined as a partial defect, the database 16 is considered as a partial-defect database. Contrarily, when the deterioration defect of the structural part 10 is determined as a uniform defect, the database 16 is considered as a uniform-defect database. The processor 14 performs the detection for the degree and the position of the deterioration defect based on FIG. 5 or FIG. 6 according to one of the aforementioned the partial-defect database or the uniform-defect database. More specifically, in the method for detecting the deterioration defect of the present disclosure, the form of the deterioration defect is determined first before the detection for the degree and the position of the deterioration defect based on FIG. 5 and/or FIG. 6 is performed, so as to raise the accuracy of determination for the degree and the position of the deterioration defect. In practice, the method and the system for detecting the deterioration defect are allowed to be applicable with other portable devices, such as tablets, smart phones, laptops, etc, so as to provide information of the real-time monitoring and the warning in advanced.

Based on the above description, in the system and the method for detecting the deterioration defect disclosed in the present disclosure, measurements are detected by the sensor and further analyzed based on time domain signals and frequency domain signals, accompanying with the utilization of the database related to the deterioration defect of the structural part, so as to provide information of the real-time monitoring and the warning in advanced for avoiding accidents of structural parts such as industrial pipelines or industrial tanks. Moreover, the system and the method for detecting the deterioration defect disclosed in the present disclosure are further applicable with the wireless transmission technology across devices to build an industrial safety monitoring platform and provide a high-performance and safe remote monitoring service.

What is claimed is:

1. A method for detecting deterioration defect of a structural part, comprising:
    detecting a waveform of time domain of the structural part by a sensor disposed on the structural part;
    performing a conversion of time domain to frequency domain for the waveform of time domain by a processor electrically connected to the sensor so as to obtain an actual modal parameter of each of a plurality of modals related to a waveform of frequency domain of the structural part;
    comparing the actual modal parameter of each of the plurality of modals to modal parameter information stored in a database to determine whether a deterioration defect exists in the structural part; and
    determining a degree and a position of the deterioration defect when the deterioration defect exists in the structural part;
    wherein the modal parameter information comprises sets of comparison modal parameters, and each of the sets of comparison modal parameters indicates a respective one of the deterioration defect of the position and other deterioration defects of other positions in the structural part.

2. The method for detecting deterioration defect of the structural part according to claim 1, wherein the actual modal parameter of each of the plurality of modals comprises an amplitude value of a characteristic frequency, each of the sets of comparison modal parameters corresponds to a plurality of first deterioration curves, and determining the degree and the position of the deterioration defect comprises comparing each of the amplitude values of the characteristic frequencies to the plurality of first deterioration curves of a respective one of the sets of comparison modal parameters so as to determine the degree and the position of the deterioration defect;
    wherein each of the plurality of first deterioration curves corresponds to a predicted deterioration defect having a deterioration defect value and located in a position of the structural part.

3. The method for detecting deterioration defect of the structural part according to claim 1, wherein the actual modal parameter of each of the plurality of modals comprises a characteristic frequency, each of the sets of comparison modal parameters comprises a plurality of second deterioration curves, and determining the degree and the position of the deterioration defect comprises:
    obtaining at least two sets of predicted deterioration defect parameters according to the characteristic frequencies of the plurality of modals and the plurality of second deterioration curves comprised in the sets of comparison modal parameters; and
    determining the degree and the position of the deterioration defect according to the at least two sets of predicted deterioration defect parameters.

4. The method for detecting deterioration defect of the structural part according to claim 3, wherein determining the degree and the position of the deterioration defect according to the at least two sets of predicted deterioration defect parameters comprising:

filtering out at least one predicted deterioration defect parameter repeated by comparing the at least two sets of predicted deterioration defect parameters;

wherein the at least one predicted deterioration defect parameter is related to the degree and the position of the deterioration defect.

5. The method for detecting deterioration defect of the structural part according to claim 1, wherein before detecting the waveform of time domain of the structural part by the sensor disposed on the structural part, the method further comprising:

determining a disposing position of the sensor on the structural part according to a characteristic frequency of each of the sets of comparison modal parameters of the database.

6. The method for detecting deterioration defect of the structural part according to claim 5, wherein a distance exists between the disposing position of the sensor and one end of the structural part, and the distance is less than or equal to ½ of a wavelength corresponding to the characteristic frequency having a greatest frequency value among the characteristic frequencies.

7. The method for detecting deterioration defect of the structural part according to claim 1, wherein the actual modal parameter of each of the plurality of modals comprises a characteristic frequency, the characteristic frequency has a first frequency in a first direction and has a second frequency in a second direction, the method for detecting deterioration defect of the structural part further comprise determining a form of the deterioration defect according to the first frequency in the first direction and the second frequency in the second direction.

8. The method for detecting deterioration defect of the structural part according to claim 7, wherein determining the form of the deterioration defect according to the first frequency in the first direction and the second frequency in the second direction comprising:

determining whether the first frequency in the first direction is consistent with the second frequency in the second direction;

determining the form of the deterioration defect as an uniform defect when the first frequency in the first direction is consistent with the second frequency in the second direction; and determining the form of the deterioration defect as an partial defect when the first frequency in the first direction is not consistent with the second frequency in the second direction.

9. The method for detecting deterioration defect of the structural part according to claim 7, wherein the database is a partial-defect database or a uniform-defect database, and the method for detecting deterioration defect of the structural part further comprises determining whether the database is the partial-defect database or the uniform-defect database according to the form of the deterioration defect.

10. The method for detecting deterioration defect of the structural part according to claim 1, wherein before detecting the waveform of time domain of the structural part by the sensor disposed on the structural part, the method for detecting deterioration defect of the structural part further comprises generating the waveform of time domain by an excitation source or fluid flowing through the structural part.

* * * * *